United States Patent
Sheu et al.

(10) Patent No.: US 12,268,784 B2
(45) Date of Patent: *Apr. 8, 2025

(54) POLYLACTIC ACID MICROSPHERE, POLYLACTIC-CO-GLYCOLIC ACID MICROSPHERE AND METHOD OF PREPARING THE SAME

(71) Applicants: Taipei Medical University, Taipei (TW); Panion & BF Biotech Inc., Taipei (TW)

(72) Inventors: Ming-Thau Sheu, Taipei (TW); Yu-Ying Hsu, Taipei (TW); Yu-De Su, Taipei (TW); Yu-Hsuan Liu, Taipei (TW); Pu-Sheng Wei, Taipei (TW)

(73) Assignees: Taipei Medical University, Taipei (TW); Panion & BF Biotech Inc., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/397,342

(22) Filed: Dec. 27, 2023

(65) Prior Publication Data

US 2024/0122856 A1 Apr. 18, 2024

Related U.S. Application Data

(63) Continuation of application No. 17/219,179, filed on Mar. 31, 2021, now Pat. No. 11,883,536.

(51) Int. Cl.
| | |
|---|---|
| *A61K 9/16* | (2006.01) |
| *A61K 9/10* | (2006.01) |
| *A61K 9/19* | (2006.01) |
| *A61K 47/10* | (2017.01) |
| *A61K 47/26* | (2006.01) |
| *A61K 47/38* | (2006.01) |

(52) U.S. Cl.
CPC ............ *A61K 9/1682* (2013.01); *A61K 9/10* (2013.01); *A61K 9/1647* (2013.01); *A61K 9/19* (2013.01); *A61K 47/10* (2013.01); *A61K 47/26* (2013.01); *A61K 47/38* (2013.01)

(58) Field of Classification Search
None
See application file for complete search history.

(56) References Cited

U.S. PATENT DOCUMENTS

2009/0169632 A1* 7/2009 Lu .................... A61K 31/70
514/23

FOREIGN PATENT DOCUMENTS

CN 111298196 A 6/2020

OTHER PUBLICATIONS

Matsumoto et al., "Drug Release Characteristics of Multi-Reservoir Type Microspheres With Poly(DL-Lactide-CO-Glycolide) and Poly(DL-Lactide)", Journal of Controlled Release 106 (2005) 172-180.

* cited by examiner

*Primary Examiner* — Melissa S Mercier
(74) *Attorney, Agent, or Firm* — McBee Moore & Vanik, IP, LLC

(57) ABSTRACT

A method of preparing polylactic acid (PLA) microsphere and polylactic-co-glycolic acid (PLGA) microsphere is provided, including the following steps. A first solution is provided, including polylactic acid or polylactic-co-glycolic acid and an organic solvent. A second solution is provided, including polyvinyl alcohol, sodium carboxymethyl cellulose and an aqueous solution. The first solution is added to the second solution and, at the same time, the second solution is agitated until polylactic acid is solidified to form a plurality of polylactic acid microspheres, or until polylactic-co-glycolic acid is solidified to form a plurality of polylactic-co-glycolic acid microspheres. The polylactic acid microspheres or polylactic-co-glycolic acid microspheres are collected. The polylactic acid microsphere and the polylactic-co-glycolic acid microsphere are respectively the accumulation of the polylactic acid and polylactic-co-glycolic acid, having a smooth surface and a mean number particle size distribution (MN) from 10 μm to 80 μm.

7 Claims, 3 Drawing Sheets

POLYLACTIC ACID MICROSPHERE, POLYLACTIC-CO-GLYCOLIC ACID MICROSPHERE AND METHOD OF PREPARING THE SAME

CROSS-REFERENCE TO RELATED APPLICATION

This application is a Continuation of U.S. application Ser. No. 17/219,179, filed on Mar. 31, 2021, which is herein incorporated by reference.

BACKGROUND

Field of Invention

The present disclosure relates to polylactic acid microspheres, polylactic-co-glycolic acid microspheres and preparation method thereof. In particular, the present disclosure relates to a preparation method for obtaining the polylactic acid microspheres and polylactic-co-glycolic acid microspheres with high production yield and better properties of injection.

Description of Related Art

At present, the main methods for preparing microspheres containing biological macromolecules are: an emulsification solvent evaporation method, an emulsification solidification method, a desolvation method, or the like.

The emulsion solvent evaporation method is prepared by mixing an aqueous solution with biological macromolecules and organic solvent, forming an emulsion by an ultrasonic method or a shaking method, and then, removing the organic solvent to obtain the microspheres by the method including a rotary evaporation method or the like. The production yield of microspheres prepared by the emulsification solvent evaporation method is lower, the risk that the organic solvent left exists, and the encapsulation rate of the microspheres for water-soluble drugs and water-soluble ingredients is poor.

Nowadays, the emulsification solidification method is generally used. The microspheres with different particle sizes and particle size distributions can be prepared according to different emulsification conditions. This method is prepared by adding an aqueous solution containing biological macromolecules to an organic solvent containing a vegetable oil or isooctane with an appropriate amount of emulsifier, forming a water-in-oil emulsion by agitating, an ultrasonic method or a membrane emulsification method, solidifying droplets by heating or a crosslinking agent (for example, formaldehyde or glutaraldehyde), and then, obtaining solidified microspheres after a separation step. However, the emulsification solidification method often causes the formed microspheres with a wider particle size distribution and uneven sizes.

Clinically, an injection containing microspheres is usually lyophilized to form powder, and reconstituted while needed. A safety risk exists if the injection is not reconstituted completely while the injection is administrated to patients. Once the microspheres have a wider particle size distribution and uneven sizes, the high risks that the time required for reconstitution will be hardly assessed, and microspheres are unevenness after reconstitution are derived. In addition, in the preparation process where the biological macromolecules are prepared as the injection nowadays, the properties of the injection (for example, property of syringes test) are often difficult to be balanced if the demand for high production yield of microspheres should be satisfied at the same time.

Therefore, it is necessary to improve the current microspheres and preparation method thereof.

SUMMARY

A method of preparing high molecular polymer microspheres is provided in some embodiments of the present disclosure, including the following steps: providing a first solution, wherein the first solution comprises a high molecular polymer and an organic solvent, wherein the organic solvent comprises dichloromethane, chloroform, ethyl acetate or a combination thereof, wherein a weight volume concentration of the high molecular polymer in the first solution is from 2.5% to 20% based on 100% by weight volume concentration of the first solution; providing a second solution, wherein the second solution comprises polyvinyl alcohol, sodium carboxymethyl cellulose and an aqueous solution, wherein a weight volume concentration of polyvinyl alcohol in the second solution is from 0.5% to 2%, and a weight volume concentration of sodium carboxymethyl cellulose in the second solution is from 0.1% to 2% based on 100% by weight volume concentration of the second solution; adding the first solution to the second solution, and at the same time, agitating the second solution until the high molecular polymer is solidified to form a plurality of high molecular polymer microspheres, in which a volume ratio of the second solution to the first solution is from 5:1 to 100:1; and collecting the plurality of high molecular polymer microspheres.

In some embodiments, the high molecular polymer is polylactic acid, polylactic-co-glycolic acid or a combination thereof.

In some embodiments, when the first solution is added to the second solution, at the same time, agitate the second solution, and the first solution is added to the second solution at a speed of from 5% to 35% of the first solution per minute based on 100% by volume of the first solution.

In some embodiments, when the first solution is added to the second solution, at the same time, agitating the second solution, the second solution is agitated at a rotation speed of from 300 rpm to 1500 rpm.

In some embodiments, the collecting the plurality of high molecular polymer microspheres comprises a centrifugal method or a sieving method.

In some embodiments, the collecting the plurality of high molecular polymer microspheres further comprises obtaining the plurality of high molecular polymer microspheres by a lyophilization method after the centrifugal method or the sieving method.

In some embodiments, a molar ratio of lactic acid to glycolic acid in polylactic-co-glycolic acid is from 85:15 to 15:85. A high molecular polymer microspheres is provided in some embodiments of the present disclosure, prepared by the following steps: providing a first solution, the first solution includes a high molecular polymer and an organic solvent, in which the organic solvent includes dichloromethane, chloroform, ethyl acetate or a combination thereof, in which a weight volume concentration of the first solution is calculated as 100%, and a weight volume concentration of the high molecular polymer in the first solution is from 2.5% to 20%; providing a second solution, in which the second solution includes polyvinyl alcohol, sodium carboxymethyl cellulose and an aqueous solution, in which a weight volume concentration of the second solution is calculated as 100%, a weight volume concentration of polyvinyl alcohol in the second solution is from 0.5% to 2%, and a weight volume concentration of sodium carboxymethyl cellulose in the second solution is from 0.1% to 2%; adding the first solution to the second solution, and at the same time, agitating the second solution until the high molecular polymer is solidified to form a plurality of high molecular polymer microspheres, in which a volume ratio of the second solution to the first solution is from 5:1 to 100:1; and collecting the plurality of high molecular polymer microspheres.

In some embodiments, the plurality of high molecular polymer microspheres are spheroid-shaped bodies, having smooth surfaces, and a mean number particle size distribution of the plurality of high molecular polymer microsphere ranges from 10 μm to 80 μm.

In some embodiments, the high molecular polymer is polylactic acid, polylactic-co-glycolic acid or a combination thereof.

An injection is provided in some embodiments of the present disclosure, prepared by the following steps: providing a first solution, in which the first solution includes a high molecular polymer and an organic solvent, in which the organic solvent includes dichloromethane, chloroform, ethyl acetate or a combination thereof, in which a weight volume concentration of the first solution is calculated as 100%, and a weight volume concentration of the high molecular polymer in the first solution is from 2.5% to 20%; providing a second solution, in which the second solution includes polyvinyl alcohol, sodium carboxymethyl cellulose and an aqueous solution, in which a weight volume concentration of the second solution is calculated as 100%, a weight volume concentration of polyvinyl alcohol in the second solution is from 0.5% to 2%, and a weight volume concentration of sodium carboxymethyl cellulose in the second solution is from 0.1% to 2%; adding the first solution to the second solution, and at the same time, agitating the second solution until the high molecular polymer is solidified to form a plurality of high molecular polymer microspheres, in which a volume ratio of the second solution to the first solution is from 5:1 to 100:1; and collecting the plurality of high molecular polymer microspheres; providing a suspension liquid, in which the suspension liquid includes a surfactant, a high molecular silicide, a sugar alcohol and a dispersant, in which the high molecular silicide includes polydimethylsiloxane; mixing the plurality of high molecular polymer microspheres and the suspension liquid to obtain a microsphere suspension liquid; and lyophilizing the microsphere suspension liquid to obtain the injection.

In some embodiments, the surfactant includes polysorbate 80, the sugar alcohol includes mannitol, and the dispersant includes sodium carboxymethyl cellulose.

In some embodiments, a weight ratio of sodium carboxymethyl cellulose to the plurality of high molecular polymer microspheres is from 1:4 to 1:10, a weight ratio of mannitol to the plurality of high molecular polymer microspheres is from 1:3 to 1:10, a weight ratio of polysorbate 80 to the plurality of high molecular polymer microspheres is from 1:60 to 1:140, and a weight ratio of polydimethylsiloxane to the plurality of high molecular polymer microspheres is from 1:80 to 1:180.

In some embodiments, the injection further includes forming an injection liquid after reconstituting the injection for 2 minutes to 10 minutes.

In some embodiments, the injection liquid passes through a 26G needle at a speed of from 0.5 mL/min to 2 mL/min.

In some embodiments, the high molecular polymer is polylactic acid, polylactic-co-glycolic acid or a combination thereof.

The method of preparing high molecular polymer microspheres is disclosed in the present disclosure, in which the high molecular polymer microspheres with a concentrated particle size distribution and smooth surfaces are prepared by the means of the specified ratio of polyvinyl alcohol and sodium carboxymethyl cellulose, served as clinical applications of injections and pharmaceutical carriers.

BRIEF DESCRIPTION OF THE DRAWINGS

In order to make the above and other objects, features, advantages and embodiments of the present invention more obvious and understandable, the accompanying drawings are described as follows.

DETAILED DESCRIPTION

In order that the present disclosure is described in detail and completeness, implementation aspects and specific embodiments of the present disclosure with illustrative description are presented, but those are not the only form for implementation or use of the specific embodiments of the present disclosure. The embodiments disclosed herein may be combined or substituted with each other in an advantageous manner, and other embodiments may be added to an embodiment without further description. In the following description, numerous specific details will be described in detail in order to enable the reader to fully understand the following embodiments. However, the embodiments of the present disclosure may be practiced without these specific details.

As used herein, unless the context specifically dictates otherwise, "a" and "the" may mean a single or a plurality. It will be further understood that "comprise", "include", "have", and similar terms as used herein indicate described features, regions, integers, steps, operations, elements and/or components, but not exclude other features, regions, integers, steps, operations, elements, components and/or groups.

Although a series of operations or steps are described below to illustrate the method disclosed herein, the order of the operations or steps is not to be construed as limiting. For example, certain operations or steps may be performed in a different order and/or concurrently with other steps. In addition, not all illustrated operations, steps, and/or features are required to implement embodiments of the present disclosure. Moreover, each of the operations or steps described herein can include a plurality of sub-steps or actions.

Figure 1:
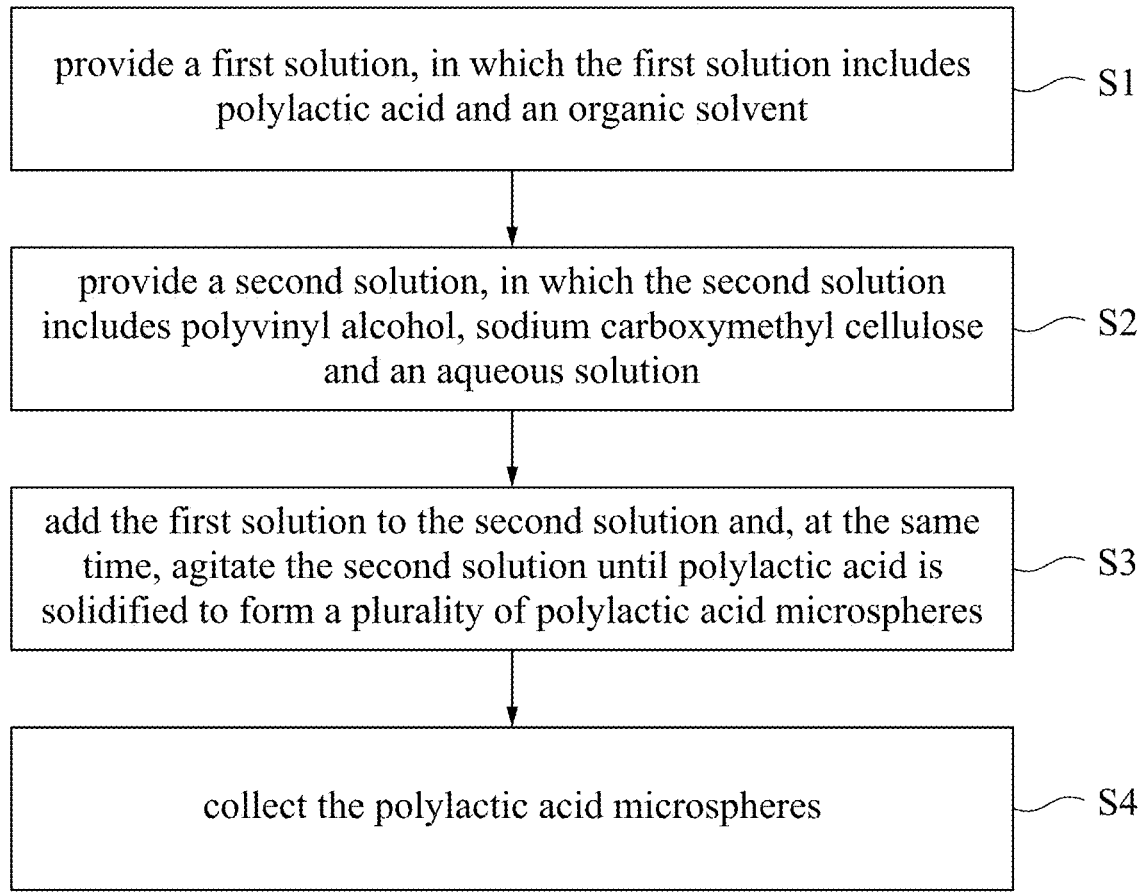
FIG. 1 illustrates a flow chart of preparing polylactic acid microspheres in one embodiment of the present disclosure.

Please refer to FIG. 1, a method of preparing polylactic acid microspheres is provided in the present disclosure, including the following steps: step S1, provide a first solution, in which a first solution includes polylactic acid and organic solvent; step S2, provide a second solution, in which the second solution includes polyvinyl alcohol, sodium carboxymethyl cellulose and an aqueous solution; step S3, add the first solution to the second solution and, at the same time, agitate the second solution until polylactic acid is solidified to form a plurality of polylactic acid microspheres; and step S4, collect polylactic acid microspheres.

In some embodiments, polylactic acid includes poly L-lactic acid, poly D-lactic acid, poly-DLlactic acid or a combination thereof. In some embodiments, the organic solvent includes dichloromethane, chloroform, ethyl acetate or a combination thereof.

In some embodiments, a weight volume concentration (w/v) of the first solution is calculated as 100%, a weight volume concentration of polylactic acid in the first solution is from 2.5% to 10%, for example, 2.5%, 3%, 4%, 5%, 6%, 7%, 8%, 9%, 10%, or any value in any interval above.

It's noted that as the weight volume concentration of the polylactic acid in the first solution increases, the production yield of the polylactic acid microspheres will generally increase, but the agglutination risk of the polylactic acid microspheres will increase, relatively. Therefore, during the preparation process, the weight volume concentration of polylactic acid in the first solution is required to be controlled within an appropriate range.

In some embodiments, the weight volume concentration of the second solution is calculated as 100%, a weight volume concentration of polyvinyl alcohol in the second solution is from 0.5% to 2%, such as 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or any value in any interval above. A weight volume concentration (w/v) of sodium carboxymethyl cellulose in the second solution, such as 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or any value in any interval above.

It's worth noting that the feature of polylactic acid microspheres having smooth surfaces can be obtained while polyvinyl alcohol and sodium carboxymethyl cellulose exist in the second solution together, in which the smoother surfaces the polylactic acid microspheres have, the less likely they agglutinate. In addition, the feature of polylactic acid microspheres having smooth surfaces can assist in the increase of the production yield of acid microspheres, for example, up to 90%.

In some embodiments, at the step of adding the first solution to the second solution, and at the same time, agitating the second solution, a volume ratio of the second solution to the first solution is from 5:1 to 100:1. In some other embodiments, the volume ratio of the second solution to the first solution is from 5:1 to 50:1, such as 5:1, 10:1, 20:1, 30:1, 40:1, 50:1, or any value in any interval above. It's should be noted that when the weight volume concentrations of polylactic acid, polyvinyl alcohol and sodium carboxymethyl cellulose are fixed at the specific values, as the volume ratio of the second solution to the first solution decreases, the agglutination risk of the polylactic acid microspheres also increases. Therefore, during the preparation process, it's important to control the volume ratio of the second solution to the first solution within an appropriate range.

In some embodiments, the step of adding the first solution to the second solution, and at the same time, agitating the second solution, can be flexibly matched with different machines and parameter settings based on the target production yield, particle size and particle size distribution of the polylactic acid microspheres. For example, a peristaltic pump (such as Thermo Fisher Scientific Dry-Bags™, USA) can be used by adding the first solution to the second solution at a rotation speed of from 25 rpm to 50 rpm, and an agitation machine (such as IKA EURO-ST 60 C S001, Germany) cab be used to agitate the second solution at a rotation speed of from 300 rpm to 1500 rpm (such as 300 rpm, 400 rpm, 500 rpm, 600 rpm, 700 rpm, 800 rpm, 900 rpm, 1000 rpm, 1100 rpm, 1200 rpm, 1300 rpm, 1400 rpm, 1500 rpm, or any value in any interval above). The main purpose of the abovementioned parameter settings are to control an appropriate and consistent speed at which the first solution is added to the second solution and a speed at which the second solution is agitated to obtain the polylactic acid microspheres having the target particle sizes and the concentrated particle size distribution and increase the production yield of polylactic acid microspheres.

Once the speed at which the first solution is add to the second solution is too quick, the agglutination risk of the polylactic acid microspheres will increase, influencing the particle sizes of polylactic acid microspheres and decreasing the production yield. The more quickly the speed of the second solution is agitated at, the greater the shear force is, and the particle sizes of polylactic acid microspheres are reduced. In particular, the main purpose of the rotation speed of from 25 rpm to 50 rpm at which the first solution is added to the second solution by the peristaltic pump is to control the addition amount per unit of time. The volume of the first solution is set as 100%, the first solution may be added to the second solution at a speed of from 5% to 35% of the first solution per minute, preferably from 5% to 15% of the first solution per minute, such as 5%, 6%, 7%, 8%, 9%, 10%, 11%, 12%, 13%, 14%, or 15% of the first solution per minute.

In some embodiments, the step of collecting polylactic acid microspheres includes a centrifugal method or a sieving method. The centrifugal method is performed by centrifuging the second solution where the polylactic acid microspheres are formed at an appropriate rotation speed (such as 2460×g), and then removing the supernatant to obtain the polylactic acid microspheres. The sieving method is performed by separating the second solution where the polylactic acid microspheres are formed by a screen with appropriate apertures to obtain the polylactic acid microspheres. In one embodiment, the step of collecting polylactic acid microspheres further includes obtaining the polylactic acid microspheres by a lyophilization method after the centrifugal method or the sieving method. The lyophilization may remove excess water and residual organic solvent and increase the stability of storage.

As the content of polyvinyl alcohol and sodium carboxymethyl cellulose increases, the viscosity of the second solution will increase, and the collection speed of the polylactic acid microspheres will decrease. In some embodiments, electrolytes (such as sodium chloride) can be added to the second solution to reduce the viscosity of the second solution and improve the collection speed of polylactic acid microspheres.

It should be emphasized that the polylactic acid microspheres obtained by the aforementioned preparation method are spheroid-shaped bodies, and the surfaces of the polylactic acid microspheres are smooth under the viewing field with magnification of 450 times to 1500 times of the electron microscope at a voltage of 5 kV. In some embodiments, the particle size D50 (the particle size corresponding to the cumulative particle size percentage of up to 50%), of the polylactic acid microspheres is from 30 μm to 55 μm, and the particle size D90 (the particle size corresponding to the cumulative particle size percentage of up to 90%) of the polylactic acid microspheres is from 60 μm to 100 μm.

A polylactic acid microsphere prepared by the steps including the abovementioned steps is also provided in the present disclosure, which is assembled by polylactic acid. The polylactic acid microspheres have smooth surfaces while observed under the viewing field with magnification of 450 times to 1500 times of the electron microscope at a voltage of 5 kV, in which the cross sections of the polylactic acid microspheres after cut are solid and smooth, and a mean number particle size distribution ranges from 10 μm to 80 μm, such as 10 μm, 20 μm, 30 μm, 40 μm, 50 μm, 60 μm, 70 μm, 80 μm, or any value in any interval above, preferably from 30 μm to 80 μm, more preferably from 35 μm to 80 μm.

An injection prepared by the following steps is further provided in the present disclosure: providing a plurality of high molecular polymer microspheres; providing a suspension liquid; mixing high molecular polymer microspheres and a suspension liquid to obtain a microsphere suspension liquid; and lyophilizing the microsphere suspension liquid to obtain the injection.

In some embodiments, the high molecular polymer microspheres are prepared by the steps similar to the abovementioned step S1 to step S4, respectively: provide a first solution, in which a first solution includes high molecular polymer and organic solvent; provide a second solution, in which the second solution includes polyvinyl alcohol, sodium carboxymethyl cellulose and an aqueous solution; add the first solution to the second solution and, at the same time, agitate the second solution until the high molecular polymer is solidified to form a plurality of high molecular polymer microspheres; and collecting the high molecular polymer microspheres. The high molecular polymer microspheres prepared by the abovementioned steps have than less reconstitution time and have better property of syringes test while prepared to form the injection than the known high molecular polymer microspheres. It should be emphasized that the abovementioned effects can only be achieved while polyvinyl alcohol and sodium carboxymethyl cellulose are included in the second solution.

In some embodiments, the high molecular polymer is polylactic acid, polylactic-co-glycolic acid or a combination thereof. In some embodiments, the suspension liquid includes a surfactant, a high molecular silicide, a sugar alcohol and a dispersant. In some embodiments, the surfactant includes sodium dodecyl sulfate (SDS), Tween-related surfactant (such as TWEEN 80), Triton-related surfactant, nonylphenol (NP)—related surfactant or a combination thereof. In some embodiments, the high molecular silicide includes polydimethylsiloxane. In some embodiments, sugar alcohol includes mannitol. In some embodiments, the dispersant includes sodium carboxymethyl cellulose. In some embodiments, the suspension liquid may include mannitol, sodium carboxymethyl cellulose, polysorbate 80, and polydimethylsiloxane. In one embodiment, a weight ratio of sodium carboxymethyl cellulose to the high molecular polymer microspheres is from 1:4 to 1:10, a weight ratio of mannitol to the high molecular polymer microspheres is from 1:3 to 1:10, a weight ratio of polysorbate 80 to the high molecular polymer microspheres is from 1:60 to 1:140, and a weight ratio of polydimethylsiloxane to the high molecular polymer microspheres is from 1:80 to 1:180. In some embodiments, as the weight ratio of sodium carboxymethyl cellulose to the high molecular polymer microspheres is from 1:5.5 to 1:10, the weight ratio of mannitol to the high molecular polymer microspheres is from 1:4 to 1:6.5, the weight ratio of polysorbate 80 to the high molecular polymer microspheres is from 1:85 to 1:130, and the weight ratio of polydimethylsiloxane to the high molecular polymer microspheres is from 1:110 to 1:175, the injection with the reconstitution time of less than 8 minutes and having great property of syringes test can be obtained.

In some embodiments, the injection is prepared by the following steps: providing a plurality of polylactic acid microspheres; providing a suspension liquid; mixing the polylactic acid microspheres and a suspension liquid to obtain a microsphere suspension liquid; and lyophilizing the microsphere suspension liquid to obtain the injection. In some embodiments, polylactic acid microspheres are prepared by the steps similar to the abovementioned step S1 to step S4, respectively: step S1, provide a first solution, in which a first solution includes polylactic acid and an organic solvent; step S2, provide a second solution, in which the second solution includes polyvinyl alcohol, sodium carboxymethyl cellulose and an aqueous solution; step S3, add the first solution to the second solution and, at the same time, agitate the second solution until polylactic acid is solidified to form a plurality of polylactic acid microspheres; and step S4, collect polylactic acid microspheres. The polylactic acid microspheres prepared by the abovementioned steps S1 to S4 have the less reconstitution time and have better property of syringes test than the known polylactic acid microspheres while prepared to form the injection. It should be emphasized that the abovementioned effects can only be achieved while polyvinyl alcohol and sodium carboxymethyl cellulose are included in the second solution.

In one embodiment, a weight ratio of sodium carboxymethyl cellulose to the polylactic acid microspheres is from 1:4 to 1:10, a weight ratio of mannitol to the polylactic acid microspheres is from 1:3 to 1:10, a weight ratio of polysorbate 80 to the polylactic acid microspheres is from 1:60 to 1:140, and a weight ratio of polydimethylsiloxane to the polylactic acid microspheres is from 1:80 to 1:180. In some embodiments, as the weight ratio of sodium carboxymethyl cellulose to the polylactic acid microspheres is from 1:5.5 to 1:10, the weight ratio of mannitol to the polylactic acid microspheres is from 1:4 to 1:6.5, the weight ratio of polysorbate 80 to the polylactic acid microspheres is from 1:85 to 1:130, and the weight ratio of polydimethylsiloxane to the polylactic acid microspheres is from 1:110 to 1:175, the injection with the reconstitution time of less than 8 minutes and having great property of syringes test can be obtained.

In some embodiments, the injection liquid is formed after the injection is reconstituted for 2 minutes to 10 minutes, and the injection liquid passes through a 26G needle (the inner diameter is about 0.26 mm, and outer diameter is about 0.46 mm) at a speed of from 0.5 mL/min to 2 mL/min.

Figure 3:
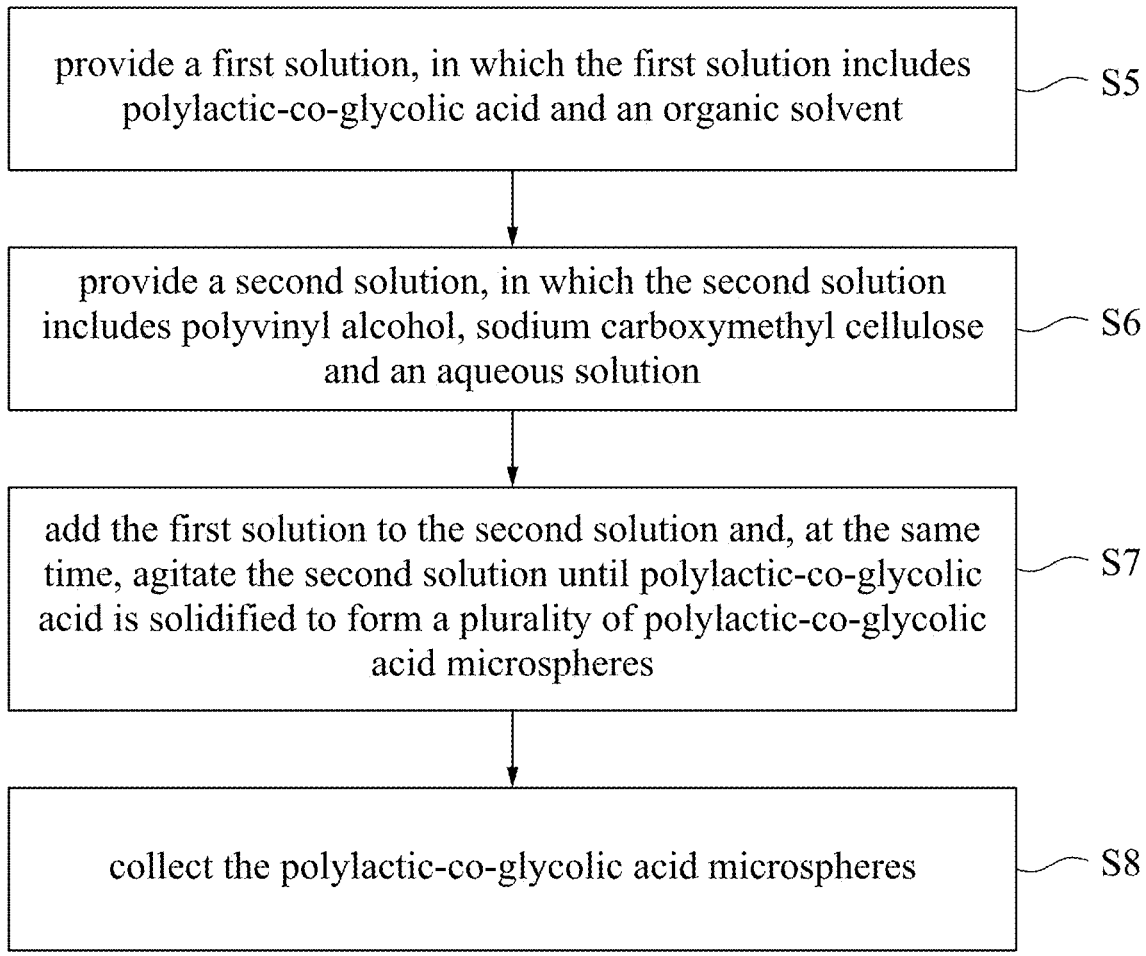
FIG. 3 illustrates a flow chart of preparing polylactic-co-glycolic acid microspheres in one embodiment of the present disclosure.

Please refer to FIG. 3. A method of preparing polylactic-co-glycolic acid (PLGA) microspheres is also provided in some embodiments of the present disclosure, including the following steps: step S5, provide a first solution, in which a first solution includes polylactic-co-glycolic acid and an organic solvent, and the organic solvent includes dichloromethane, chloroform, ethyl acetate or a combination thereof, and a weight volume concentration (w/v) of the first solution is calculated as 100%, a weight volume concentration of polylactic-co-glycolic acid in the first solution is from 2.5% to 20% (such as 2.5%, 3%, 4%, 5%, 6%, 7%, 8%, 9%, 10%, 11%, 12%, 13%, 14%, 15%, 16%, 17%, 18%, 19%, 20%, or any value in any interval above); step S6, provide a second solution, in which the second solution includes polyvinyl alcohol, sodium carboxymethyl cellulose and an aqueous solution, in which a weight volume concentration (w/v) of the second solution is calculated as 100%, a weight volume concentration of polyvinyl alcohol in the second solution is from 0.5% to 2%, such as 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or any value in any interval above, and a weight volume concentration of sodium carboxymethyl cellulose in the second solution is from 0.1% to 2% (such as 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or any value in any interval above); step S7, add the first solution to the second solution, and at the same time, agitate the second solution until polylactic-co-glycolic acid is solidified to form a plurality of polylactic-co-glycolic acid microspheres, in which a volume ratio of the second solution to the first solution is from 5:1 to 100:1 (such as 5:1, 10:1, 20:1, 30:1, 40:1, 50:1, 60:1, 70:1, 80:1, 90:1, 100:1, or any value in any interval above); and step S8, collect polylactic-co-glycolic acid microspheres.

Furthermore, the appropriate ranges of the parameter settings for preparing polylactic-co-glycolic acid microspheres can be adjusted based on the similar consideration factors of the abovementioned method of preparing polylactic acid microspheres in the present disclosure. For example, as the weight volume concentration of polylactic-co-glycolic acid in the first solution is higher, the production yield of polylactic-co-glycolic acid microspheres will generally increase, but the agglutination risk of polylactic-co-glycolic acid microspheres will increase, relatively, and as the volume ratio of the second solution to the first solution decreases, the agglutination risk of polylactic-co-glycolic acid microspheres also increases. Therefore, the ranges of the weight volume concentration of polylactic-co-glycolic acid in the first solution, the volume ratio of the second solution to the first solution, or the like, have specific effects. In addition, the different machines and parameter settings can be flexibly matched based on the target production yield, particle size and particle size distribution of polylactic-co-glycolic acid microspheres.

In some embodiments, a molar ratio of lactic acid to glycolic acid in polylactic-co-glycolic acid is from 85:15 to 15:85, such as 85:15, 80:20, 75:25, 70:30, 65:35, 60:40, 55:45, 50:50, 45:55, 40:60, 35:65, 30:70, 25:75, 20:80, 15:85, or any molar ratio in any interval above. It can be understood that because of the structure differences between glycolic acid and lactic acid (glycolic acid is more hydrophilic), the polylactic-co-glycolic acid microspheres prepared by polylactic-co-glycolic acid may be degraded more easily in biological bodies than the polylactic acid microspheres. In addition, as the molar ratio of glycolic acid in polylactic-co-glycolic acid increases, the corresponding polylactic-co-glycolic acid microspheres will be degraded more easily in biological bodies.

In some embodiments, at the step of adding the first solution to the second solution, and at the same time, agitating the second solution, a peristaltic pump can be used by adding the first solution to the second solution at a rotation speed of from 25 rpm to 50 rpm for the main purpose of controlling addition amount per unit of time. The volume of the first solution is set as 100%, the first solution may be added to the second solution at a speed of from 5% to 35% of the first solution per minute, preferably from 5% to 15% of the first solution per minute, such as 5%, 6%, 7%, 8%, 9%, 10%, 11%, 12%, 13%, 14%, or 15% of the first solution per minute added. In some embodiments, the step of adding the first solution to the second solution, and at the same time, agitating the second solution is performed by agitating the second solution at a rotation speed of from 300 rpm to 1500 rpm (such as 300 rpm, 400 rpm, 500 rpm, 600 rpm, 700 rpm, 800 rpm, 900 rpm, 1000 rpm, 1100 rpm, 1200 rpm, 1300 rpm, 1400 rpm, 1500 rpm, or any value in any interval above).

In some embodiments, the step of collecting polylactic-co-glycolic acid microspheres includes a centrifugal method or a sieving method. The centrifugal method is performed by centrifuging the second solution where the polylactic-co-glycolic acid microspheres are formed at an appropriate rotation speed (such as 2460×g), and then removing the supernatant to obtain the polylactic-co-glycolic acid microspheres. The sieving method is performed by separating the second solution where the polylactic-co-glycolic acid microspheres are formed by a screen with appropriate apertures to obtain polylactic-co-glycolic acid microspheres. In one embodiment, the step of collecting polylactic-co-glycolic acid microspheres further includes obtaining the polylactic-co-glycolic acid microspheres by a lyophilization method after the centrifugal method or the sieving method. The lyophilization may remove excess water and residual organic solvent and increase the stability of storage.

A polylactic-co-glycolic acid microsphere provided in some embodiments is prepared by the following steps: provide a first solution, in which a first solution includes polylactic-co-glycolic acid and an organic solvent, in which the organic solvent includes dichloromethane, chloroform, ethyl acetate or a combination thereof, in which a weight volume concentration of the first solution is calculated as 100%, a weight volume concentration of polylactic-co-glycolic acid in the first solution is from 2.5% to 20% (such as 2.5%, 3%, 4%, 5%, 6%, 7%, 8%, 9%, 10%, 11%, 12%, 13%, 14%, 15%, 16%, 17%, 18%, 19%, 20%, or any value in any interval above); provide a second solution, in which the second solution includes polyvinyl alcohol, sodium carboxymethyl cellulose and an aqueous solution, in which a weight volume concentration of the second solution is calculated as 100%, a weight volume concentration of polyvinyl alcohol in the second solution is from 0.5% to 2%, such as 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or any value in any interval above, and a weight volume concentration (w/v) of sodium carboxymethyl cellulose in the second solution is from 0.1% to 2%, such as 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or any value in any interval above; add the first solution to the second solution, and at the same time, agitate the second solution until polylactic-co-glycolic acid is solidified to form a plurality of polylactic-co-glycolic acid microspheres, in which a volume ratio of the second solution to the first solution is from 5:1 to 100:1, such as 5:1, 10:1, 20:1, 30:1, 40:1, 50:1, 60:1, 70:1, 80:1, 90:1, 100:1, or any value in any interval above; and collect polylactic-co-glycolic acid microspheres.

In some embodiments, the polylactic-co-glycolic acid microspheres are spheroid-shaped bodies, having a smooth surface, and a mean number particle size distribution of the polylactic-co-glycolic acid microsphere ranges from 10 μm to 80 μm, such as 10 μm, 20 μm, 30 μm, 40 μm, 50 μm, 60 μm, 70 μm, 80 μm, or any value in any interval above. In some embodiments, the particle size D10 (the particle size corresponding to the cumulative particle size percentage of up to 10%) of the polylactic-co-glycolic acid microspheres is from 1 μm to 30 μm, the particle size D50 (the particle size corresponding to the cumulative particle size percentage of up to 50%) is from 10 μm to 55 μm, and the particle size D90 (the particle size corresponding to the cumulative particle size percentage of up to 90%) is from 15 μm to 100 μm.

A method of preparing high molecular polymer microspheres is provided in the present disclosure, including the following steps: provide a first solution, in which a first solution includes a high molecular polymer and an organic solvent in which the organic solvent includes dichloromethane, chloroform, ethyl acetate or a combination thereof, in which a weight volume concentration of the first solution is calculated as 100%, a weight volume concentration of the high molecular polymer in the first solution is from 2.5% to 20%; provide a second solution, the second solution includes polyvinyl alcohol, sodium carboxymethyl cellulose and an aqueous solution, in which a weight volume concentration of the second solution is calculated as 100%, a weight volume concentration of polyvinyl alcohol in the second solution is from 0.5% to 2%, and a weight volume concentration of sodium carboxymethyl cellulose in the second solution is from 0.1% to 2%; add the first solution to the second solution, and at the same time, agitate the second solution until the high molecular polymer is solidified to form a plurality of high molecular polymer microspheres, in which a volume ratio of the second solution to the first solution is from 5:1 to 100:1; and collect the high molecular polymer microspheres. It can be understood that the high molecular polymer microspheres can be prepared by the steps or according to the ranges the same as or similar to the abovementioned steps or ranges for preparing polylactic acid microspheres or preparing polylactic-co-glycolic acid microspheres. In some embodiments, the high molecular polymer is polylactic acid, polylactic-co-glycolic acid or a combination thereof.

A high molecular polymer microsphere is provided in the present disclosure, preparing by the following steps: provide a first solution, in which a first solution includes a high molecular polymer and an organic solvent, in which the organic solvent includes dichloromethane, chloroform, ethyl acetate or a combination thereof, in which a weight volume concentration of the first solution is calculated as 100%, a weight volume concentration of the high molecular polymer in the first solution is from 2.5% to 20%; provide a second solution, the second solution includes polyvinyl alcohol, sodium carboxymethyl cellulose and an aqueous solution, in which a weight volume concentration of the second solution is calculated as 100%, a weight volume concentration of polyvinyl alcohol in the second solution is from 0.5% to 2%, and a weight volume concentration of sodium carboxymethyl cellulose in the second solution is from 0.1% to 2%; add the first solution to the second solution, and at the same time, agitating the second solution until the high molecular polymer is solidified to form a plurality of high molecular polymer microspheres, in which a volume ratio of the second solution to the first solution is from 5:1 to 100:1; and collect the high molecular polymer microspheres. It can be understood that the high molecular polymer microspheres can be prepared by the steps or according to the ranges the same as or similar to the abovementioned steps or ranges for preparing polylactic acid microspheres or preparing polylactic-co-glycolic acid microspheres. In some embodiments, the high molecular polymer is polylactic acid, polylactic-co-glycolic acid or a combination thereof.

To further confirm the improved properties of the formed polylactic acid microspheres and polylactic-co-glycolic acid microspheres in various embodiments of the present disclosure, the following tests were performed. It should be noted that the following examples were illustrative only for providing exemplary purposes, and not to limit the present invention.

Example 1. Preparation Method of Polylactic Acid Microspheres

The specific preparation conditions of the polylactic acid microspheres were shown in Table 1 below.

First of all, prepare a disperse phase (first solution) and a continuous phase (second solution). The disperse phase was obtained by adding polylactic acid (PLA) to dichloromethane (DCM), and the continuous phase was obtained by adding polyvinyl alcohol (PVA) and sodium carboxymethyl cellulose (SCMC) to water and mixing polyvinyl alcohol (PVA) and sodium carboxymethyl cellulose (SCMC) in water. The concentrations of the disperse phase and the continuous phase were expressed in percentage (%) by weight volume concentration (w/v).

Next, the disperse phase was added to the continuous phase by a peristaltic pump (Thermo Fisher Scientific Dry-Bags™ Simple Peristaltic Pump Starter Pack, USA), and the disperse phase and the continuous phase were agitated to form a mixing liquor by a mixer (IKA EURO-60 C ST S001, Germany), and the rotation speed unit was revolution (s) per minute (rpm). Although four different agitation conditions, divided into Group A to group D (see Table 1 below), were used in the preparation of the polylactic acid microspheres in this example. However, one of ordinary skills in the art could flexibly adjust parameter settings based on the properties of different machines.

During the agitation process, polylactic acid was solidified to form the polylactic acid microspheres since dichloromethane, the organic solvent, would volatilize. Finally, centrifuge the mixing liquor at 2460×g for ten minutes to collect the polylactic acid microspheres, and lyophilize the polylactic acid microspheres to remove excess water and residual organic solvent for storage conveniently.

TABLE 1

Table of preparation conditions of polylactic acid microspheres

| Group | Disperse phase PLA (g) | Disperse phase PLA (g)/DCM (mL) (w/v; %) | Continuous phase 0.5%(w/v) PVA/Water + 1%(w/v)SCMC/Water (mL) | Continuous phase:Disperse phase volume ratio (v/v) | Peristaltic pump (rpm) | Paddle mixer Rotation speed (rpm) | Torque (Ncm) |
|---|---|---|---|---|---|---|---|
| A | 15 | 6 | 2500 | 10:1 | 50 | 400 | — |
| B | | | | | 25 | 400 | 5~7 |
| C | | | | | 50 | 500 | 8.5~11.5 |
| D | | | | | 25 | 500 | 9~11 |

Example 2. Preparation Method of Injection

Next, the polylactic acid microspheres obtained by four different preparation conditions (A-D) in Example 1 were prepared as a microsphere suspension liquid according to the formula a in Table 2 below, and then the microsphere suspension liquid was lyophilized to prepare the injection. In addition, in purpose of testing the differences between the different injection formulations at the same time, the polylactic acid microspheres of group C in Table 1 was selected and prepared to be the microsphere suspension liquids according to the formula b and the formula c of the following Table 2, respectively. The microsphere suspension liquids were lyophilized to be prepared to be the injections. The specific preparation process was performed as follows.

First, 300 mL of the aqueous solution containing polysorbate 80 (TWEEN 80), polydimethylsiloxane (dimethicone), D-mannitol, and sodium carboxymethyl cellulose (SCMC) was added to the lyophilized polylactic acid microspheres, and mixed uniformly to form the microsphere suspension liquid. Then, the microsphere suspension liquid was lyophilized to obtain the injection. The lyophilization may remove excess water, and the injection was reconstituted while needed, increasing the stability of storage.

TABLE 2

Formula table of microsphere suspension liquid

| | PLA (mg) | SCMC (mg) | D-Mannitol (mg) | TWEEN 80 (mg) | Dimethicone (mg) |
|---|---|---|---|---|---|
| Formula a | 150 | 35 | 47 | 2.35 | 1.76 |
| Formula b | 150 | 26.25 | 35.25 | 1.76 | 1.32 |
| Formula c | 150 | 17.5 | 23.5 | 1.18 | 0.88 |

Example 3, Characteristics of Polylactic Acid Microspheres and Injection

Figure 2A:
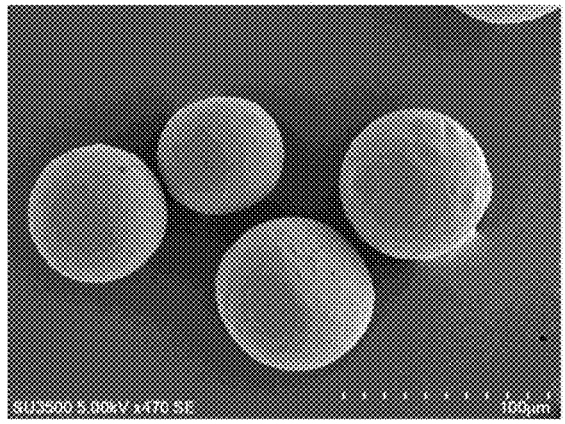
FIGS. 2A to 2D illustrate electron microscope images in one embodiment of the present disclosure.
Figure 2B:
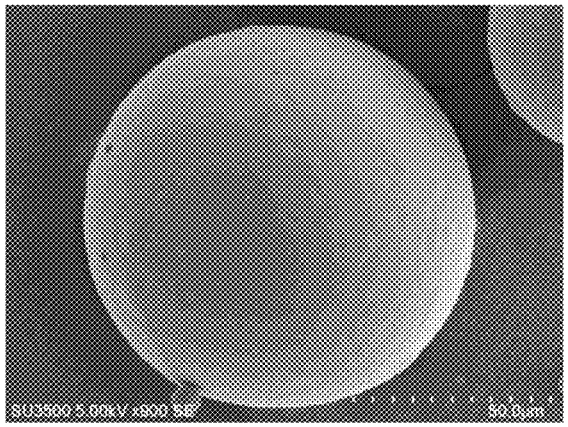
Figure 2C:
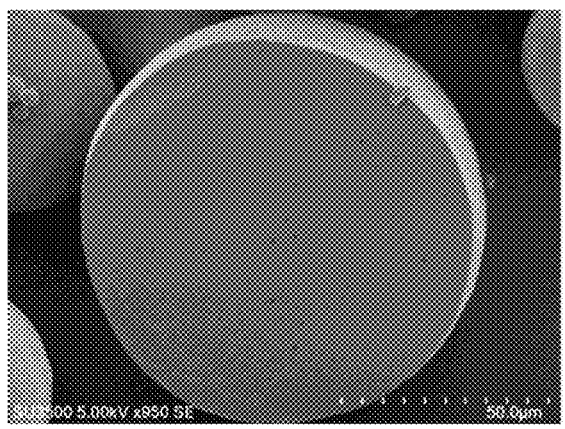
Figure 2D:
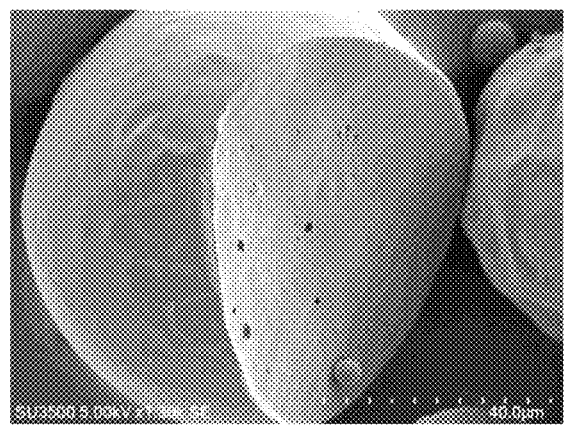

In order to further understand the characteristics of the polylactic acid microspheres and the injections obtained by the preparation method of Example 1 and Example 2, first, observe the appearances of the polylactic acid microspheres with the electron microscope, under the viewing field with magnification of 450 times to 1500 times and at a voltage of 5 kV. Please see FIG. 2A to FIG. 2D (the digital value of the proportional scale at the lower right corner of each figure is the length corresponding to the sum of the line segment of the proportional scale), FIG. 2A to FIG. 2D were the viewing fields with magnification of 470 times, 900 times, 950 times and 1300 times, respectively, and the surfaces of the polylactic acid microspheres were smooth. In addition, FIG. 2O and FIG. 2D showed the internal structures of the polylactic acid microspheres after cut were solid and smooth sections.

Next, calculate the production yield and the particle size distribution of the polylactic acid microspheres prepared by Group A to Group D of Example 1, and compare the difference of the reconstitution time, anti-agglutination after reconstitution and property of syringes test between the injections prepared in Example 2 and the commercial products 1 and 2. The results were shown in Table 3 below.

TABLE 3

Comparison table of injections and commercial products 1 and 2

| | Group | Production yield of polylactic acid microspheres (%) | Reconstitution time | Particle size D50/D90 (μm) | | anti-agglutination | Injection speed (mL/min) | | |
|---|---|---|---|---|---|---|---|---|---|
| | | | | | | | 0.5 | 1 | 2 |
| Commercial product | 1 | — | 2 hours | — | | 1 | — | ++ | x | x |
| | 2 | — | 8 mins | — | 1 | | + | + | x |
| Injection of the present disclosure (preparation conditions of Example 1/ Formulas of microsphere suspension liquid of Example 2) | A/a | 92.94 | 8 mins | 49.44/80.33 | 1.35 15.49 | + | x | x |
| | B/a | 91.52 | 8 mins | 51.06/85.17 | 1.17 13.42 | + | + | ++ |
| | C/a | 91.57 | 8 mins | 38.06/68.67 | 1.47 16.94 | ++ | ++ | ++ |
| | D/a | 91.58 | 8 mins | 43.36/79.99 | 1.31 15.10 | ++ | ++ | ++ |
| | C/b | 91.57 | 3 mins | 38.06/68.67 | — — | ++ | ++ | ++ |
| | C/c | 91.57 | 3 mins | 38.06/68.67 | — — | ++ | ++ | ++ |

In the field symbols of this table, "—" was represented as untested, "x" in the injection speed field was represented as unpassable, "+" was represented as unsmooth in the syringes test, and "++" was represented as smooth in the syringes test.

In the production yield of the polylactic acid microspheres, the added amount of polylactic acid (i.e., the weight of polylactic acid added for preparing the disperse phase of Example 1) was calculated as 100%, and the percentage of the weight of the final polylactic acid microspheres after finishing the preparation, including after the lyophilization, was calculated. The results were shown in Table 3 (production yield of the polylactic acid microspheres). The preparation method of the present disclosure increased the production yield of the polylactic acid microspheres up to more than 90%.

The particle size analysis of the polylactic acid microspheres was performed using a laser particle size analyzer (Beckman Coulter LS 200, USA) at room temperature. The results were shown in Table 3 (particle size). D50 of the polylactic acid microspheres in the present disclosure was from 30 μm to 55 μm, and D90 was from 60 μm to 100 μm.

The reconstitution time was calculated by the time of the reconstitution required to be completed, in which the reconstitution was performed by adding the injection prepared in Example 2 and the commercial products 1 and 2 to 5 mL of redistilled water (ddH$_2$O), respectively. The results were shown in Table 3 (reconstitution time). Compared with the commercial products 1 and 2, the injection obtained by the present disclosure had a shorter reconstitution time, that is, a faster reconstitution speed.

The testing method for anti-agglutination was shown as follows. First, reconstitute the injections prepared in Group A to Group D of Example 1, the commercial product 1 and the commercial product 2 with 5 mL of redistilled water to form the injection liquids, and lyophilizing 1 mL of the injection liquid obtained from the same position point and centrifugated at 48×g for 30 seconds in an electric centrifugal machine. Then, the contents of polylactic acid of the commercial products 1 and 2 at the fixed points of the injection liquids were served as denominators, respectively, and the ratios of polylactic acid of the injection liquids prepared by Group A to D of Example 1 of the present disclosure at the fixed points to polylactic acid of the commercial products 1 and 2 at the fixed points of the injection liquids were calculated. The higher ratio represented the better anti-agglutination. The results were shown in Table 3 (anti-agglutination), and the anti-agglutination of the injections in the present disclosure was better than the commercial products 1 and 2.

As used herein, "property of syringe test" represents the property that the injection can pass through the needle cylinder and the needle without sticking to the barrel wall of the needle cylinder and without blocking the needle. The testing method was as follows. The injections of the present disclosure, the commercial products 1 and 2 after the lyophilization were added to 5 mL of redistilled water for reconstitution, followed by obtaining 1 mL of which to test property of syringe test at different flow rates of the shots by 26G needles. The results demonstrated the property of syringe test of the injections in the present disclosure was equivalent to which of the commercial products 1 and 2 while reconstituted to be the injection liquids and injected at the injection speed of 0.5 mL/min, and while injected at the faster injection speed (1 mL/min and 2 mL/min), the injections of the present disclosure had the better property of syringe test compared with the commercial products 1 and 2.

Example 4, Preparation Method of Polylactic-Co-Glycolic Acid Microspheres

In this example, polylactic-co-glycolic acid was replaced with polylactic acid in Example 1 and served as the material of the disperse phase. The polylactic-co-glycolic acid microspheres were prepared according to the conditions of Table 4. The preparation process was basically similar to Example 1, and the difference was that a stir was used in the agitation of this example, replacing the paddle mixer.

First of all, prepare a disperse phase (first solution) and a continuous phase (second solution). The disperse phase was obtained by adding polylactic-co-glycolic acid (PLGA) to dichloromethane (DCM), in which a molar ratio of lactic acid to glycolic acid was 25:75. The continuous phase was obtained by adding polyvinyl alcohol (PVA) and sodium carboxymethyl cellulose (SCMC) to water and mixing polyvinyl alcohol (PVA) and sodium carboxymethyl cellulose (SCMC) in water. Likewise, the concentrations of the disperse phase and the continuous phase were expressed in percentage (%) by weight volume concentration (w/v).

Next, the disperse phase was added to the continuous phase by a peristaltic pump (Thermo Fisher Scientific Dry-Bags™ Simple Peristaltic Pump Starter Pack, USA), and the disperse phase and the continuous phase were agitated to form a mixing liquor by a stir at an agitation rate with a rotation speed unit of 850 rpm. One of ordinary skills in the art could flexibly adjust parameter settings based on the properties of different machines.

During the agitation process, polylactic-co-glycolic acid was solidified to form the polylactic-co-glycolic acid microspheres since dichloromethane, the organic solvent, would volatilize. Finally, centrifuge the mixing liquor at 2460×g for ten minutes to collect the polylactic-co-glycolic acid microspheres, and lyophilize the polylactic-co-glycolic acid microspheres to remove excess water and residual organic solvent for storage conveniently.

TABLE 4

Table of preparation conditions of polylactic-co-glycolic acid microspheres

| Group | Disperse phase PLGA (g)/DCM (mL) (w/v; %) | DCM (mL) | Continuous phase 0.5%(w/v) PVA/water + 1% (w/v) SCMC/water (mL) | Condition Speed of stir (rpm) | Particle size (μm) D10 | D50 | D90 |
|---|---|---|---|---|---|---|---|
| A | 5 | 3 | 30 | 850 | 2.82 | 12.51 | 19.86 |
| B | 10 | | | | 16.79 | 31.64 | 43.28 |
| C | 15 | | | | 21.60 | 50.20 | 78.23 |

With respect to polylactic acid used in Example 1, polylactic-co-glycolic acid was used to replace polylactic acid and served as the material of the disperse phase for preparing the microspheres in the present example. The polylactic-co-glycolic acid microspheres of Example 4 could also be served as injections or pharmaceutical carriers, and polylactic-co-glycolic acid microspheres had a faster degradation speed in biological bodies than the polylactic acid microspheres of Example 1.

The specific ratios of polyvinyl alcohol and sodium carboxymethyl cellulose in the continuous phase were used in some embodiments of the present disclosure to prepare the polylactic acid microspheres with a concentrated particle size distribution and having smooth surfaces. In addition. the production yield of the polylactic acid microspheres obtained by the preparation method was up to 90%. Compared with the commercial products, the injection of the present disclosure not only shortens the reconstitution time, but also has better anti-agglutination and property of syringes test, which can increase clinical applications. Furthermore, polylactic-co-glycolic acid is served as the material of the disperse phase in other embodiments of the present disclosure, and the polylactic-co-glycolic acid microspheres with faster degradation speed are produced by using the preparation method similar to the aforementioned method of preparing the polylactic acid microspheres.

The polylactic acid microspheres and the polylactic-co-glycolic acid microspheres, with different degradation speeds, can be obtained by adjusting the material of the disperse phase in the preparation method in some embodiments of the present disclosure, which can be served as injections or pharmaceutical carriers and enhance convenience of the preparation.

Although the present invention has been disclosed in the above embodiments, it is not intended to limit the present invention. Anyone familiar with this technique can make various changes and modifications without departing from the spirit and scope of the present invention. The scope of protection of the invention shall be subjected to the scope of appended claims.

What is claimed is:

1. A method of preparing high molecular polymer microspheres, comprising:
   providing a first solution, wherein the first solution comprises a high molecular polymer and an organic solvent, wherein the organic solvent comprises dichloromethane, chloroform, ethyl acetate or a combination thereof, wherein a weight volume concentration of the high molecular polymer in the first solution is from 2.5% to 20% based on 100% by weight volume concentration of the first solution;
   providing a second solution, wherein the second solution comprises polyvinyl alcohol, sodium carboxymethyl cellulose and an aqueous solution, wherein a weight volume concentration of polyvinyl alcohol in the second solution is from 0.5% to 2%, and a weight volume concentration of sodium carboxymethyl cellulose in the second solution is from 0.1% to 2% based on 100% by weight volume concentration of the second solution;
   adding the first solution to the second solution, and at the same time, agitating the second solution until the high molecular polymer is solidified to form a plurality of high molecular polymer microspheres, wherein a volume ratio of the second solution to the first solution is from 5:1 to 100:1; and
   collecting the plurality of high molecular polymer microspheres.

2. The method of claim 1, wherein the high molecular polymer is polylactic acid, polylactic-co-glycolic acid or a combination thereof.

3. The method of claim 1, wherein the second solution consists of polyvinyl alcohol, sodium carboxymethyl cellulose and an aqueous solution.

4. The method of claim 1, wherein when the first solution is added to the second solution, at the same time, agitating the second solution, the second solution is agitated at a rotation speed of from 300 rpm to 1500 rpm.

5. The method of claim 1, wherein the collecting the plurality of high molecular polymer microspheres comprises a centrifugal method or a sieving method.

6. The method of claim 5, wherein the collecting the plurality of high molecular polymer microspheres further comprises obtaining the plurality of high molecular polymer microspheres by a lyophilization method after the centrifugal method or the sieving method.

7. The method of claim 2, wherein a molar ratio of lactic acid to glycolic acid in polylactic-co-glycolic acid is from 85:15 to 15:85.

* * * * *